United States Patent
Horio et al.

(10) Patent No.: US 7,532,937 B2
(45) Date of Patent: May 12, 2009

(54) ARTIFICIAL INNER EAR AND THERMOELECTRIC GENERATOR THEREFOR

(75) Inventors: Yuma Horio, Hamamatsu (JP); Takahisa Tachibana, Hamamatsu (JP); Junya Suzuki, Iwata (JP); Satoshi Iwasaki, Hamamatsu (JP)

(73) Assignee: Yamaha Corporation, Shizuoka-ken (JP)

( * ) Notice: Subject to any disclaimer, the term of this patent is extended or adjusted under 35 U.S.C. 154(b) by 661 days.

(21) Appl. No.: 11/340,503

(22) Filed: Jan. 27, 2006

(65) Prior Publication Data

US 2006/0169314 A1 Aug. 3, 2006

(30) Foreign Application Priority Data

Jan. 31, 2005 (JP) ............................ P2005-022347

(51) Int. Cl.
*A61N 1/05* (2006.01)
*H01L 35/30* (2006.01)

(52) U.S. Cl. ........................................ 607/57; 136/205
(58) Field of Classification Search ................... 136/205
See application file for complete search history.

(56) References Cited

U.S. PATENT DOCUMENTS

2002/0156509 A1 10/2002 Cheung

FOREIGN PATENT DOCUMENTS

JP 10-111368 4/1998

*Primary Examiner*—Carl H Layno
*Assistant Examiner*—Yun Haeng Lee
(74) *Attorney, Agent, or Firm*—Dickstein Shapiro LLP

(57) ABSTRACT

An artificial inner ear includes a speech processor that operates based on electricity generated by a thermoelectric transducer module, in which numerous thermoelectric elements join between oppositely arranged upper and lower substrates each having numerous electrodes. A heat absorption layer composed of a heat conductive material such as a resin, rubber, and metal is attached to the upper substrate of the thermoelectric transducer module. The heat absorption layer has deformability in shape in conformity with a prescribed part of the human body and is heated using human body temperature so as to cause a temperature difference between the upper and lower substrates, thus generating electricity in the thermoelectric transducer module. A heat-dissipation member composed of aluminum can be attached to the lower substrate so as to increase the temperature difference.

12 Claims, 6 Drawing Sheets

ARTIFICIAL INNER EAR AND THERMOELECTRIC GENERATOR THEREFOR

BACKGROUND OF THE INVENTION

1. Field of the Invention

The present invention relates to thermoelectric generators including thermoelectric transducer modules for generating electricity using biologically generated heat such as human body heat. The present invention also relates to artificial inner ears using thermoelectric generators.

This application claims priority on Japanese Patent Application No. 2005-22347, the content of which is incorporated herein by reference.

2. Description of the Related Art

Conventionally, various types of thermoelectric transducer modules performing thermoelectric conversion based on the Peltier effect and Seebeck effect have been developed and used for heating/cooling devices and generators, for example. A typical type of thermoelectric transducer module is designed in such a way that numerous thermoelectric elements are fixed and arranged between a pair of insulating substrates, wherein numerous electrodes are formed at prescribed positions of the oppositely arranged surfaces of the paired insulating substrates, and upper and lower ends of thermoelectric elements respectively join the electrodes oppositely arranged each other by way of solder. Japanese Patent Application Publication No. H10-111368 discloses an example of a thermoelectric wristwatch using a thermoelectric transducer module.

In the aforementioned thermoelectric wristwatch, a thermoelectric transducer module is attached to the interior surface of a rear cover by way of a plate spring, and a heat-dissipation ring connected to a booster circuit is attached to the surface opposite to the surface directly brought into contact with the plate spring in association with the thermoelectric transducer module. When a user uses a thermoelectric wristwatch attached on his/her wrist in such a way that the rear cover is directly brought into contact with the skin surface, the user's body heat (i.e., body heat) is transmitted to the thermoelectric transducer module via the rear cover and the plate spring, so that the thermoelectric transducer module converts the user's body heat into electricity. Hence, the thermoelectric wristwatch operates by use of the electricity generated by the thermoelectric transducer module.

The aforementioned thermoelectric wristwatch has a drawback in that the heat transmission efficiency thereof is deteriorated because of the intervention of the relatively thick rear cover and plate spring that are arranged between the user's skin surface and the thermoelectric transducer module. In addition, the heat-dissipation ring is arranged outside of the casing of the thermoelectric wristwatch, so that the heat exchange efficiency thereof is deteriorated due to the external temperature, which makes it difficult to produce a relatively large temperature difference between the terminal ends of thermoelectric elements included in the thermoelectric transducer module. This causes difficulty in increasing the amount of electricity generated by the thermoelectric transducer module. Furthermore, the rear cover of the thermoelectric wristwatch is not flexible and therefore cannot be deformed in shape to suit the user's skin surface. That is, it is very difficult to adequately bring the rear cover into close contact with the user's skin surface. This also causes difficulty in increasing the amount of electricity generated by the thermoelectric transducer module.

Moreover, there is a high demand to develop artificial small-size inner ears that can adequately operate based on electricity generated using biologically generated heat such as human body heat.

SUMMARY OF THE INVENTION

It is an object of the present invention to provide a thermoelectric generator realized by a thermoelectric transducer module that is improved in heat transmission efficiency and that can generate a relatively large amount of electricity.

It is another object of the present invention to provide an artificial inner ear using a thermoelectric generator that can generate electricity by use of biologically generated heat such as human body heat.

A thermoelectric generator of the present invention includes a thermoelectric transducer module in which numerous thermoelectric elements join between oppositely arranged upper and lower substrates each having numerous electrodes, wherein the upper substrate is heated using human body heat so as to cause a temperature difference between the upper and lower substrates, thus generating electricity. A heat absorption layer composed of a heat conductive material having deformability in shape in conformity with the skin surface of a prescribed part of a human body is attached onto the upper substrate. This increases an overall contact area between the heat absorption layer and the skin surface of the prescribed part of the human body, thus increasing an amount of heat being transmitted to the upper substrate from the skin surface. Hence, it is possible to increase the amount of electricity generated by the thermoelectric transducer module.

In addition, a heat-dissipation member composed of a prescribed metal is attached to the lower substrate of the thermoelectric transducer module, thus further increasing a temperature difference between the upper and lower substrates. Therefore, it is possible to generate a relatively great amount of electricity. Specifically, the heat-dissipation member is composed of aluminum or aluminum alloy, and it can be connected with heat-dissipation wires for efficient dissipation of heat from the lower substrate.

The heat absorption layer includes at least one of a resin layer of 5 mm or less thickness, a rubber layer of 5 mm or less thickness, and a metal layer of 500 μm or less thickness, wherein it is possible to appropriately combine these layers. When the heat absorption layer is constituted by laminating two or more layers composed of different materials, it is possible to realize desired heat absorption characteristics as well as desired shape and thickness for the heat absorption layer. When the heat absorption layer is composed of resin materials, it is possible to use plastics, nitrile resin, and ethylene resin, for example. When the heat absorption layer is composed of a prescribed metal, it is preferable to reduce the thickness therefor, thus preventing the user's skin surface from being damaged and thus preventing the user from feeling uncomfortable.

The aforementioned heat absorption layer can be used to form the upper substrate of the thermoelectric transducer module. This reduces the amount of materials used for the formation of the thermoelectric transducer module; and this simplifies the overall structure of the thermoelectric generator. In this case, it is preferable that the heat absorption layer have a relatively large thickness because a planar surface directly connected to terminal ends of thermoelectric elements can be maintained even when the heat absorption layer deforms in conformity with the skin surface of the prescribed part of the human body.

The thermoelectric generator further includes a battery for accumulating electricity generated by the thermoelectric transducer module. This realizes effective use of the electricity generated based on the human body heat.

An artificial inner ear of the present invention is constituted by a microphone for picking up sound in the surroundings, a speech processor for performing speech processing so as to convert the sound into audio signals, a transmitter for transmitting audio signals, a receiver, implanted into a human head, for receiving audio signals, and an electrode, implanted into a cochlea, for applying an electric impulse to an auditory nerve in response to audio signals so as to make a human brain sensitive to the sound. The aforementioned thermoelectric generator serves as a power source for the speech processor. This realizes a compact-size artificial inner ear having small dimensions; and this also realizes an easy-to-handle artificial inner ear, because the speech processor operates using a lightweight power source.

The artificial inner ear is adapted to a human body (e.g., a human head portion) in such a way that the speech processor equipped with the thermoelectric generator is attached to a prescribed portion of the human body (e.g., an arm) by way of a fitting member (e.g., a belt and a hook) while the heat absorption layer is brought into close contact with the prescribed portion of the human body. Herein, it is possible to use a belt for attaching the speech processor to the human body, such as on an arm. In addition, it is possible to use a hook for tightening the belt for attaching the speech processor to the human body via clothes.

BRIEF DESCRIPTION OF THE DRAWINGS

These and other objects, aspects, and embodiments of the present invention will be described in more detail with reference to the following drawings, in which.

DESCRIPTION OF THE PREFERRED EMBODIMENT

This invention will be described in further detail by way of examples with reference to the accompanying drawings.

Figure 1:
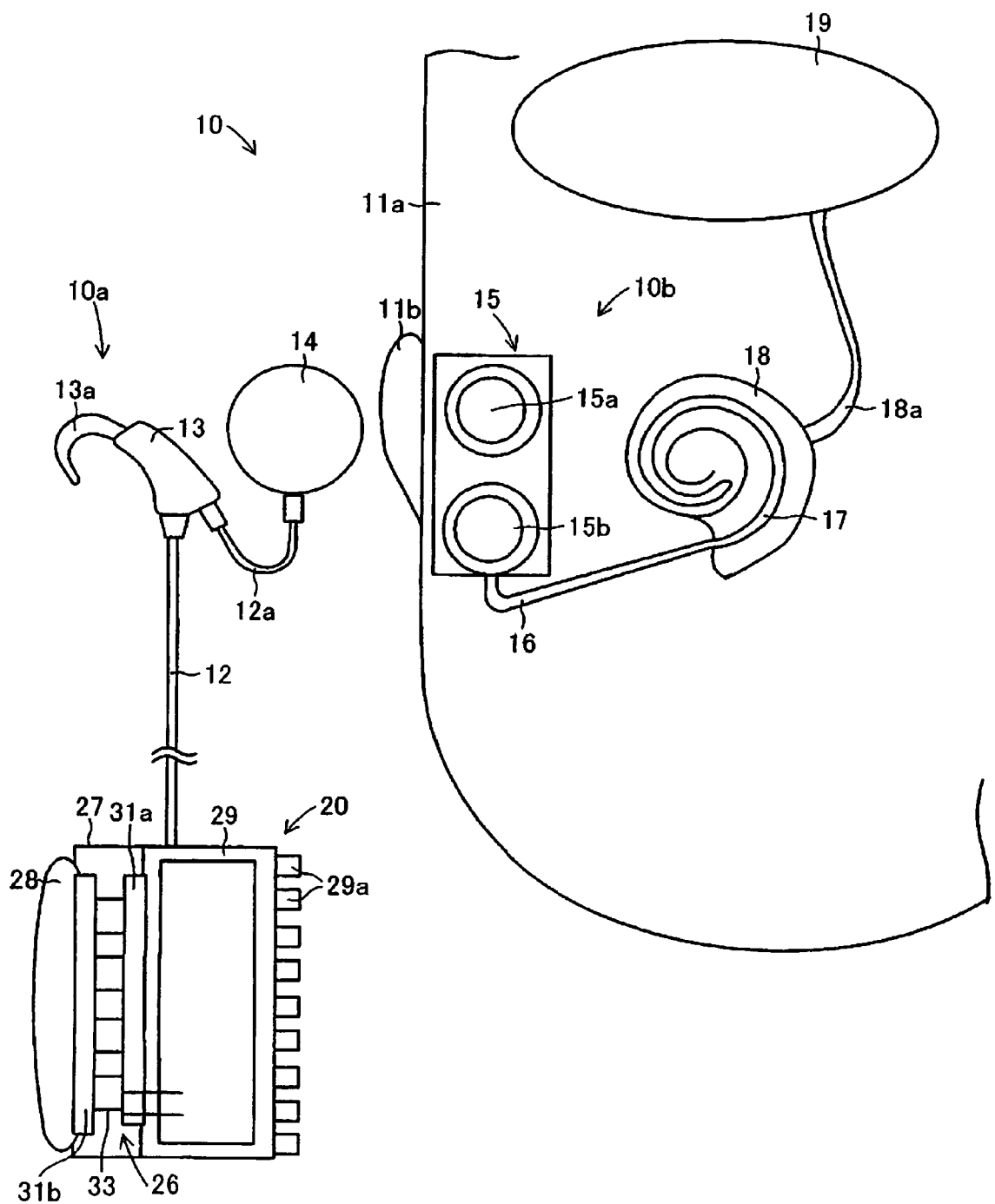
FIG. 1 diagrammatically shows an artificial inner ear attached onto a human head in accordance with a preferred embodiment of the present invention.
Figure 2:
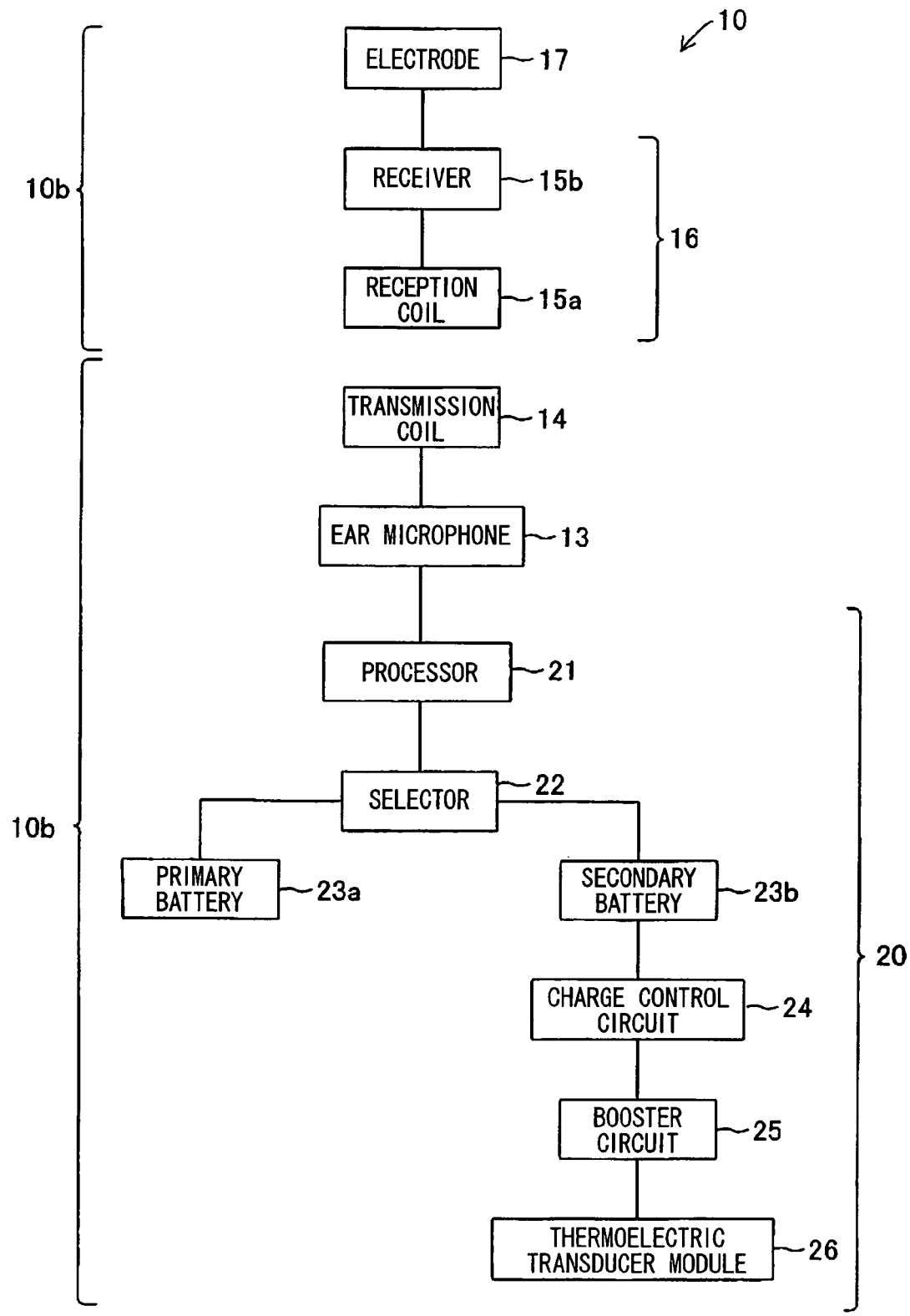
FIG. 2 is a block diagram showing essential blocks incorporated into the artificial inner ear.

FIGS. 1 and 2 show the overall system configuration for an internal ear 10 in accordance with a preferred embodiment of the present invention. The internal ear 10 (see FIG. 11) is constituted by an external unit 10a that is arranged outside of a human body 11 and an internal unit 10b that is implanted into a head 11a of the human body 11. The external unit 10a is constituted by a speech processor 20 (including a thermoelectric generator for generating electricity based on the heat given off by the human body 11), a ear microphone 13 connected to the speech processor 20 via a cable 12, and a transmission coil 14 connected to the ear microphone 13 via a cable 12a.

The internal unit 10b is constituted by a reception device 15 having a reception coil 15a and a receiver 15b, and an electrode 17 connected to the reception device 15 via a cable 16 with respect to a prescribed number of channels. The reception device 15 is implanted into the head 11 a of the human body 11 by way of a surgical operation at a prescribed position in proximity to an ear 11b. The electrode 17 is inserted into a cochlea 18, by which it applies electrical impulses to an auditory nerve 18a. The cochlea 18 is connected to a brain 19 via the auditory nerve 18a.

The ear microphone 13 has an ear hook 13a having an approximately semispherical shape, whereby by hooking the ear hook 13a on the ear 11b of the head 11a, it is possible to attached the ear microphone 13 onto the head 11a. Both the transmission coil 14 and the reception device 15 include magnets (not shown), whereby when the ear hook 13a is hooked on the ear 11b of the head 11a, and the transmission coil 14 is attracted towards the reception device 15 so that it is fixed at a prescribed position opposite to the reception device 15 via the surface skin layer of the head 11a.

The artificial inner ear 10 of the present embodiment is designed such that the ear microphone 13 picks us sound in the surroundings thereof, and the sound is subjected to the speech processing in the speech processor 20 so as to produce coded audio information. The transmission coil 14 serves as an antenna so as to transmit the audio information in the form of wireless signals, which are then received by the reception coil 15 a of the reception device 15 implanted into the head 11a. The received wireless signals are sent to the receiver 15b in which they are sent to the electrode 17 with respect to a prescribed channel, which is used for the audio reception. Thus, the electrode 17 allows electric current to flow into the auditory nerve 18 via the prescribed channel. Hence, an electric impulse is applied from the auditory nerve 18 to the brain 19, which is thus made sensitive to the sound.

Figure 3:
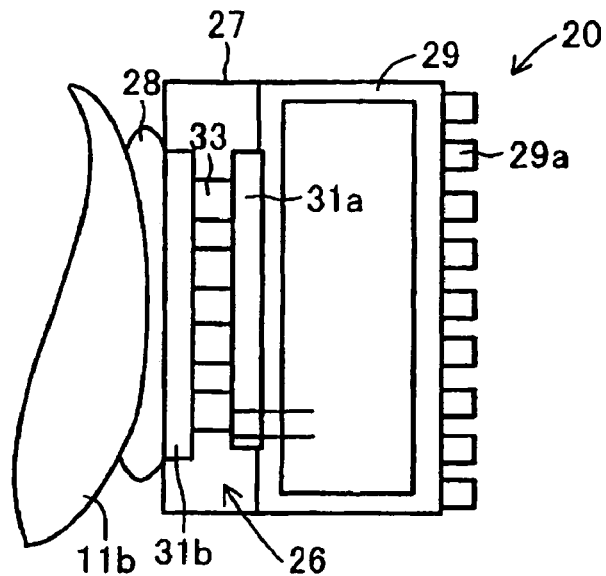
FIG. 3 diagrammatically shows the exterior of a speech processor that is provided externally of the human head in association with the artificial inner ear.

As shown in FIG. 2, the speech processor 20 includes a processor 21, a selector 22, a primary battery 23a, a secondary battery 23b, a charge control circuit 24, a booster circuit 25, and a thermoelectric transducer module 26. The speech processor 20 is designed as shown in FIG. 3 such that the thermoelectric module 26 and its associated parts are incorporated into a housing 27 having a box-like shape composed of heat insulating material. Specifically, the thermoelectric transducer module 26 is attached to the housing 27 in such a way that a prescribed surface (lying in a heat-absorption side) thereof slightly projects externally from the housing 27. Hence, a heat absorption layer 28 composed of soft polyethylene is attached to the heat-absorption surface of the thermoelectric transducer module 26.

A prescribed surface of a heat-dissipation member 29 having a box-like shape composed of aluminum is fixed onto another surface (lying on a heat-dissipation side) of the thermoelectric transducer module 26. Another surface of the heat-dissipation member 29 is exposed externally from the housing 27. In addition, a plurality of heat-dissipation fins corresponding to projections are formed on the exposed surface of the heat-dissipation member 29. FIG. 3 does not include illustrations regarding the processor 21, selector 22, primary battery 23a, secondary battery 23b, charge control circuit 24, and booster circuit 25, all of which are incorporated into the heat-dissipation member 29.

Figure 4:
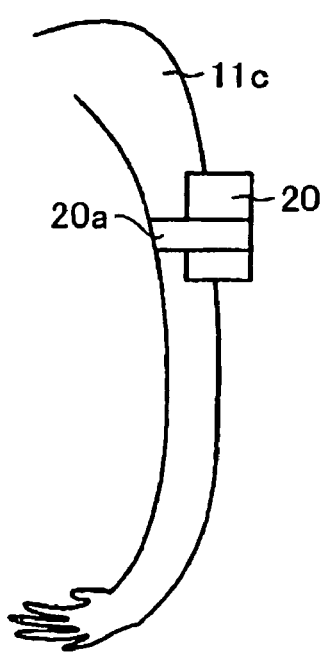
FIG. 4 shows the speech processor attached onto a human arm.

As shown in FIG. 4, the speech processor 20 has a belt 20a, which is wound about an arm 11c of the human body so as to fix it to the arm 11c. In this case, the speech processor 20 is fixed to the arm 11c in such a way that the heat absorption layer 28 is brought into contact with the skin surface. In addition, the heat absorption layer 28 deforms in shape to suit the skin surface of the arm 11c. Therefore, when the speech processor 20 is attached to the arm 11c, the overall surface of the heat absorption layer 28 may be substantially brought into contact with the skin surface of the arm 11c.

Details of the thermoelectric transducer module 26 will be described with reference to FIGS. 5 and 6. The thermoelectric transducer module 26 has a pair of insulating substrates consisting of a lower substrate 31a and an upper substrate 31b. Numerous lower electrodes 32a are attached on the upper surface of the lower substrate 31a at prescribed positions, and numerous upper electrodes 32b are attached to the lower surface of the upper substrate 31b at prescribed positions. Incidentally, FIG. 5 does not show these electrodes 32a and 32b. The lower substrate 31 a and the upper substrate 31b are integrally united by way of numerous thermoelectric elements 33 formed by chips, wherein the lower ends of the thermoelectric elements 33 are respectively fixed to the lower electrodes 32a via solder, and the upper ends are respectively fixed to the upper electrodes 32b via solder.

In the above, the lower electrodes 32a and the upper electrodes 32b are arranged opposite to each other with prescribed distances, each corresponding to one thermoelectric element 33, therebetween. Each of the upper electrodes 32b attached to the upper substrate 31b joins the upper ends of the two thermoelectric elements 33 positioned adjacent to each other. In contrast, the lower electrodes 32a attached to the lower substrate 31 a are divided into two groups, wherein each of the lower electrodes 32a belonging to a first group joins the lower end of a single thermoelectric element 33, and each of the lower electrodes 32a belonging to a second group joins the lower ends of the two thermoelectric elements 33 positioned adjacent to each other. Specifically, the lower electrodes 32a of the first group are arranged in two corners in the right side of the lower substrate 31a (see FIG. 5) and are respectively connected with leads 34a and 34b at one terminal thereof, thus making them accessible to a chargeable battery or an external device.

Both the lower substrate 31a and the upper substrate 31b are formed using plates composed of alumina; and the thermoelectric elements 33 having rectangular parallelepiped shapes include P-type and N-type elements. The thermoelectric elements 33 are arranged between the lower substrate 31a and the upper substrate 31b and are electrically connected together by way of the lower electrodes 32a and the upper electrodes 32b. Each of the P-type thermoelectric elements 33 is composed of bismuth-antimony-tellurium alloy, and each of the N-type thermoelectric elements 33 is composed of bismuth-antimony-tellurium-selenium alloy. The P-type elements and N-type elements are alternately arranged between the lower substrate 31a and the upper substrate 31b.

The thermoelectric transducer module 26 has prescribed dimensions, i.e., left-right and front-back widths of 65 mm, and height of 3.0 mm. In addition, the thermoelectric transducer module 26 is composed of a material having property Z, which is defined as $3.0 \times 10^{-3}$ $K^{-1}$. Furthermore, the thickness of the heat absorption layer 28 is set to 5 mm. The thermoelectric transducer module 26 having the aforementioned dimensions is installed in the speech processor 20 in such a way that the upper substrate 31b thereof forms the heat absorption side and is directed towards the heat absorption layer 28. The heat of the human body 11 is transmitted via the arm 11c and is then absorbed by way of the heat absorption layer 28, so that the upper substrate 31b is heated. That is, the thermoelectric transducer module 26 generates electricity in response to a temperature difference occurring between the upper substrate 31b being heated and the lower substrate 31a not being heated.

The lower substrate 31a is equipped with the heat-dissipation member 29 having heat-dissipation fins 29a, wherein heat is dissipated from the heat-dissipation member 29 and the heat-dissipation fins 29a, so that the lower substrate 31a of the thermoelectric transducer module 26 is cooled. This increase the temperature difference between the lower substrate 31 a and the upper substrate 31b. As a result, it is possible to further increase the electricity generated by the thermoelectric transducer module 26. The terminal ends of the leads 34a and 34b run through the wall of the heat-dissipation member 29 and are connected to the booster circuit 25, which is installed in the heat-dissipation member 29. The booster circuit 25 increases the electricity of the thermoelectric transducer module 26, which is supplied thereto via the leads 34a and 34b, so that the increased electricity is supplied to the secondary battery 23b by way of the charge control circuit 24.

The secondary battery 23b is a chargeable lithium battery. The charge control circuit 24 controls the voltage at a prescribed level with respect to the increased electricity of the booster circuit 25, which is then supplied to the secondary battery 23b. The secondary battery 23b accumulates the electricity supplied thereto from the charge control circuit 24. The primary battery 23a is a disposable alkali battery. The selector 22 is configured using a switch so as to switch over the connection with respect to the processor 21, so that the electricity of the primary battery 23a or the electricity of the secondary battery 23b is selectively supplied to the processor 21.

The processor 21 serves as a control section for the speech processor 20 so as to perform speech processing on sound picked up by the ear microphone 13. The aforementioned drawings do not show details of the speech processor 20 other than the aforementioned parts, but the speech processor 20 contains various operators, controls, and buttons such as a power switch as well as a display or an indicator for emitting light to show remaining power values of the primary battery 23a and the secondary battery 23b.

As described above, the thermoelectric generator of the present embodiment, which operates using the human body heat, is basically constituted by the thermoelectric transducer module 26, heat absorption layer 28, heat-dissipation member 29, and heat-dissipation fins 29a.

When the artificial inner ear 10 having the aforementioned constitution is adapted to the human body 11, the speech processor 20 is fixed onto the arm 11c by tightening the belt 20a in the condition where the heat absorption layer 28 is brought in close contact with the skin surface of the arm 11c. This makes it possible for the heat of the arm 11c (due to the heat of the human body 11) to be directly transmitted to the heat absorption layer 28, by which most of the heat absorbed by the heat absorption layer 28 is transmitted to the upper substrate 31b of the thermoelectric transducer module 26. As a result, the upper ends of the thermoelectric elements 33 lying close to the upper substrate 31b are heated.

The lower substrate 31a of the thermoelectric transducer module 26 is not placed to directly absorb the heat of the human body 11 and is cooled due to the heat dissipation realized by the heat-dissipation member 29 and the heat-dissipation fins 29a. This produces relatively large temperature differences between the lower ends of the thermoelectric elements 33 lying close to the lower substrate 31a and the upper ends of the thermoelectric elements 33 lying close to the upper substrate 31b. Hence, the thermoelectric transducer module 26 generates electricity in response to the temperature differences. Thus, the secondary battery 23b is charged. In this state, the ear microphone 13 is attached to the ear 11b, and the transmission coil 14 is positioned in proximity to the reception device 15 already implanted into the head 11a. Then, the selector 22 is turned to establish connection between the processor 21 and the secondary battery 23b, and the power switch is turned on.

Thus, the speech processor 20 starts operating so that sound and voices in the surroundings are picked up by the ear microphone 13 and are converted into electric signals, which are then transmitted to the internal section 10b so as to make the brain 19 sensitive to sound and voices. Due to the continuous working of the artificial inner ear 10 for a prescribed time period, when the charged value of the secondary battery 23b decreases to make the speech processor 20 inoperable, the selector 22 is turned again so as to establish connection between the primary battery 23a and the processor 21. Hence, the speech processor 20 can continue working due to the electricity supplied from the primary battery 23a. In this state, the secondary battery 23b is charged due to the electricity generated by the thermoelectric transducer module 26 using the heat of the human body 11.

As described above, the artificial inner ear 10 of the present embodiment is characterized by using the "deformable" heat absorption layer 28, which can be deformed in shape in conformity with the skin surface of the arm 11c and which is attached onto the upper substrate 31b of the thermoelectric transducer module 26 for generating electricity for the speech processor 20. The heat absorption layer 28 is brought into close contact with the skin surface of the arm 11c, thus increasing the amount of heat absorbed by the upper substrate 31b of the thermoelectric transducer module 26 via the skin surface of the arm 11c. This noticeably increases the amount of electricity generated by the thermoelectric transducer module 26; hence, the speech processor 20 can operate in a stable manner.

In addition, the artificial inner ear 10 of the present embodiment is characterized in that the heat-dissipation member 29 composed of aluminum and the heat-dissipation fins 29a are formed on the lower substrate 31a of the thermoelectric transducer module 26. This increases a temperature difference between the lower substrate 31a and the upper substrate 31b; hence, the thermoelectric transducer module 26 can generate a relatively great amount of electricity. The speech processor 20 incorporates the secondary battery 23b that can accumulate the electricity generated by the thermoelectric transducer module 26; hence, it is possible to effectively use the electricity generated by the thermoelectric transducer module 26 without wasting it.

Furthermore, the speech processor 20 has a specially designed power source using a thermoelectric generator operable based on biological heat (e.g., human body heat) incorporating the aforementioned thermoelectric transducer module 26; hence, it is possible to reduce the overall weight of the speech processor 20. The speech processor 20 uses the primary battery 23a, which is an auxiliary power source and can be easily replaced with new one. This may greatly reduce the work necessary for the replacement of battery. That is, any user can handle the speech processor 20 with ease. The belt 20a allows the speech processor 20 to be easily attached to the arm 11c in an appropriate manner.

The present embodiment can be modified in a variety of ways with regard to a speech processor that is externally arranged in proximity to the user's body.

Figure 7:
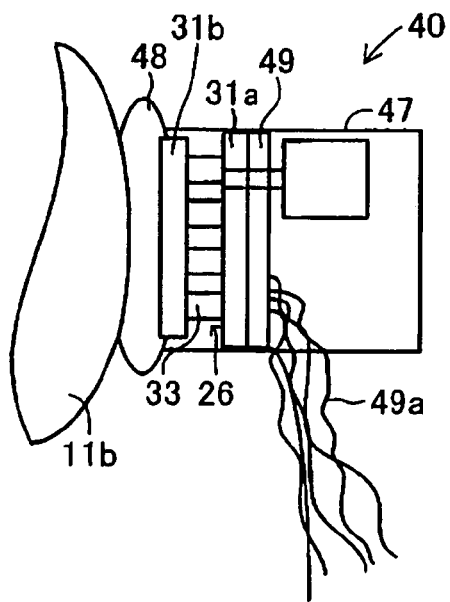
FIG. 7 shows the exterior appearance partly in cross section showing a speech processor adapted to the artificial inner ear in accordance with a first modification of the present embodiment.

FIG. 7 shows a speech processor 40 adapted to the artificial inner ear 10 in accordance with a first modification of the present invention. Unlike the aforementioned speech processor 20, the speech processor 40 does not have the box-shaped heat-dissipation member 29 and the heat-dissipation fins 29a. Instead, the speech processor 40 has a plate-shaped heat-dissipation member 49 composed of aluminum and heat-dissipation wires 49a. In addition, a prescribed surface area of a housing 47 of the speech processor 40 has an opening allowing the installation of a heat absorption layer 48 composed of soft rubber of 5 mm thickness, which projects therefrom.

FIG. 7 shows the external appearance of the speech processor 40, which is attached to the arm 11c and which is viewed from the. lower side; hence, the illustration of FIG. 7 corresponds to the lower surface of the housing 47. A hole (not shown) is formed to allow the heat-dissipation wires 49a to be extended from the exterior of the speech processor 40. Except the aforementioned hole, the overall surface of the housing 47 is continuous. Other constituent elements of the speech processor 40 are designed to be identical to those of the aforementioned speech processor 20. In the speech processor 40, the other parts identical to those shown in the speech processor 20 incorporated into the artificial inner ear 10 are designated by the same reference numerals and are not described in detail.

The speech processor 40 is characterized in that the heat absorption layer 48 is composed of soft rubber; hence, similar to with the speech processor 20, it is possible to efficiently absorb heat from the arm 11c by way of the upper substrate 31b of the thermoelectric transducer module 26. In addition, the heat of the lower substrate 31a is dissipated to the exterior by way of the plate-shaped heat-dissipation member 49 and the heat-dissipation wires 49a. This increases temperature differences between both terminal ends of the thermoelectric elements 33; hence, the thermoelectric transducer module 26 can generate a relatively great amount of electricity. Other operation and effects of the speech processor 40 are similar to those of the aforementioned speech processor 20 adapted to the artificial inner ear 10.

Figure 8:
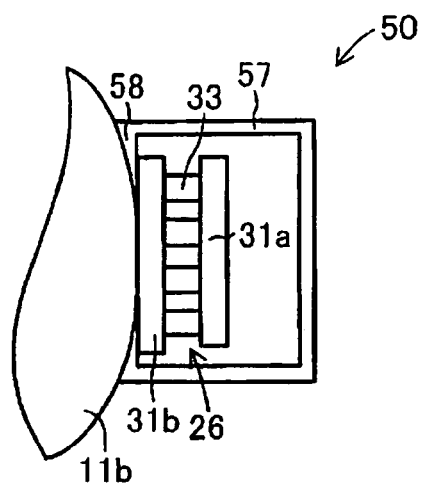
FIG. 8 shows the exterior appearance partly in cross section showing a speech processor adapted to the artificial inner ear in accordance with a second modification of the present embodiment.

FIG. 8 shows a speech processor 50 adapted to the artificial inner ear 10 in accordance with a second modification of the present embodiment. The speech processor 50 does not have the box-shaped heat-dissipation member 29 and heat-dissipation fins 29a, attached to the speech processor 20, or the plate-shaped heat-dissipation member 49 and heat-dissipation wires 49a, attached to the speech processor 40. In addition, the exterior of the speech processor 50 is formed using a box-shaped housing 57 having no opening, in which the upper substrate 31b of the thermoelectric transducer module 26 is fixed to a prescribed interior surface thereof.

Specifically, the thermoelectric transducer module 26 is fixed to a wall 58 whose thickness is 500 μm or less in the housing 57; in other words, the maximal thickness of the wall 58 is set to 500 μm or so. The wall 58 is formed using a heat absorption layer composed of aluminum. The exterior surface of the wall 58 is formed to have a prescribed curvature in conformity with the skin surface of the arm 11c. Specifically, the center area of the wall 58 is reduced in thickness in comparison with its side end areas; hence, the overall exterior surface of the wall 58 is shaped to be brought into close contact with the skin surface of the arm 11c. Other constituent elements of the speech processor 50 are identical to those of the aforementioned speech processor 20 adapted to the artificial inner ear 10.

A thermoelectric generator adapted to the speech processor 50 is constituted by the thermoelectric transducer module 26 and the wall 58 serving as the heat absorption layer. In comparison with the aforementioned thermoelectric generators adapted to the speech processors 20 and 40, the thermoelectric generator adapted to the speech processor 50 may generate slightly less electricity. However, the speech processor 50 as a whole can be reduced in dimensions, realizing a compact scale and light weight. That is, the second modification provides an easy-to-handle device easily attached to the arm 11c. Other operation and effects of the speech processor 50 are similar to those of the aforementioned speech processors 20 and 40 respectively adapted to the artificial inner ear 10.

Figure 9:
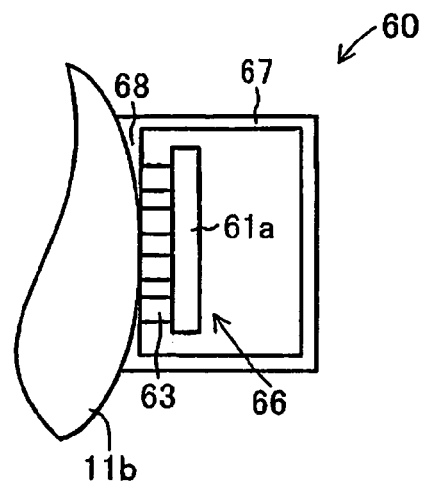
FIG. 9 shows the exterior appearance partly in cross section showing a speech processor adapted to the artificial inner ear in accordance with a third modification of the present embodiment.

FIG. 9 shows a speech processor 60 adapted to the artificial inner ear 10 in accordance with a third modification of the present invention. In the speech processor 60, an upper substrate of a thermoelectric transducer module 66 forms a side wall 68 of a housing 67. The thermoelectric transducer module 66 does not have an upper substrate (corresponding to the aforementioned upper substrate 31b of the thermoelectric transducer module 26), but upper electrodes (not shown) are formed on the side wall 68 of the housing 67. That is, the thermoelectric transducer module 66 is configured using thermoelectric elements 63 such that the upper ends of the thermoelectric elements 63 are fixed to the upper electrodes formed on the side wall 68 of the housing 67, and the lower ends of the thermoelectric elements 63 are fixed to lower electrodes (not shown) formed on a lower substrate 61a.

The housing 67 is composed of magnesium alloy, and the thickness of the side wall 68 is 500 μm or less, in other words, the maximal thickness of the side wall 68 is set to 500 μm or so. The side wall 68 formed the upper substrate of the thermoelectric transducer module 66 and serves as a heat absorption layer as well. The side wall 68 has a curvature in conformity with the skin surface of the arm 11c; that is, the center portion thereof is reduced in thickness in comparison with the side ends thereof. Other constituent elements of the speech processor 60 are identical to those of the aforementioned speech processor 50 adapted to the artificial inner ear.

Since the aforementioned thermoelectric generator (i.e., the thermoelectric transducer module 66) for generating electricity for the speech processor 60 does not require the upper substrate, it is possible to reduce the amount of materials in manufacturing and to simplify the structure thereof. The other operation and effects of the speech processor 60 are similar to those of the speech processor 50 adapted to the artificial inner ear 10.

Figure 10:
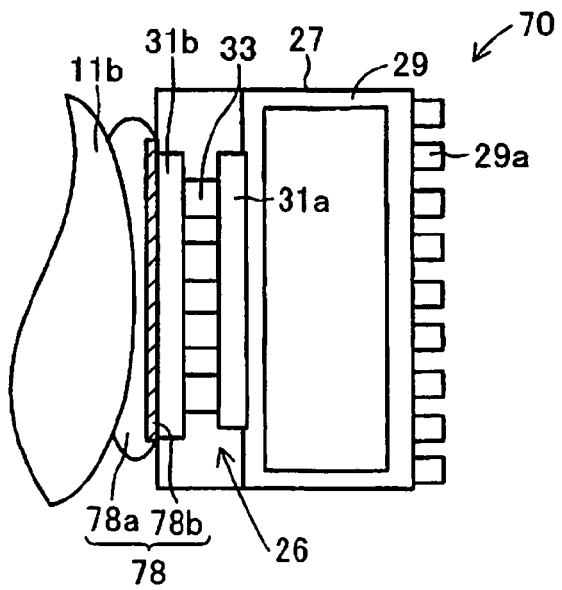
FIG. 10 shows the exterior appearance partly in cross section showing a speech processor adapted to the artificial inner ear in accordance with a fourth modification of the present embodiment.

FIG. 10 shows a speech processor 70 adapted to the artificial inner ear 10 in accordance with a fourth modification of the present embodiment. The speech processor 70 is equipped with a heat absorption layer 78, which is constituted by a soft plastic layer 78a of 2.5 mm thickness and an aluminum layer 78b of 250 μm thickness. The aluminum layer 78b is covered with the plastic layer 78a, which thus forms the exterior surface of the heat absorption layer 78. Other constituent elements of the speech processor 70 are identical to those of the speech processor 20 adapted to the artificial inner ear 10.

The fourth modification is characterized in that the soft plastic layer 78a is brought directly into contact with the skin surface, and the aluminum layer 78b (i.e., a metal layer having a high thermal absorption coefficient) is arranged inside of the heat absorption layer 78; hence, it is possible to efficiently absorb heat without damaging the skin of the arm 11c and without making the user uncomfortable. Due to the aforementioned structure of the heat absorption layer 78 (formed by the combination of different materials, i.e., the plastic layer 78a and the aluminum layer 78b), it is possible for the speech processor 70 to have a high degree of freedom in design. Other operation and effects of the speech processor 70 are similar to those of the speech processor 20 adapted to the artificial inner ear 10.

Figure 11:
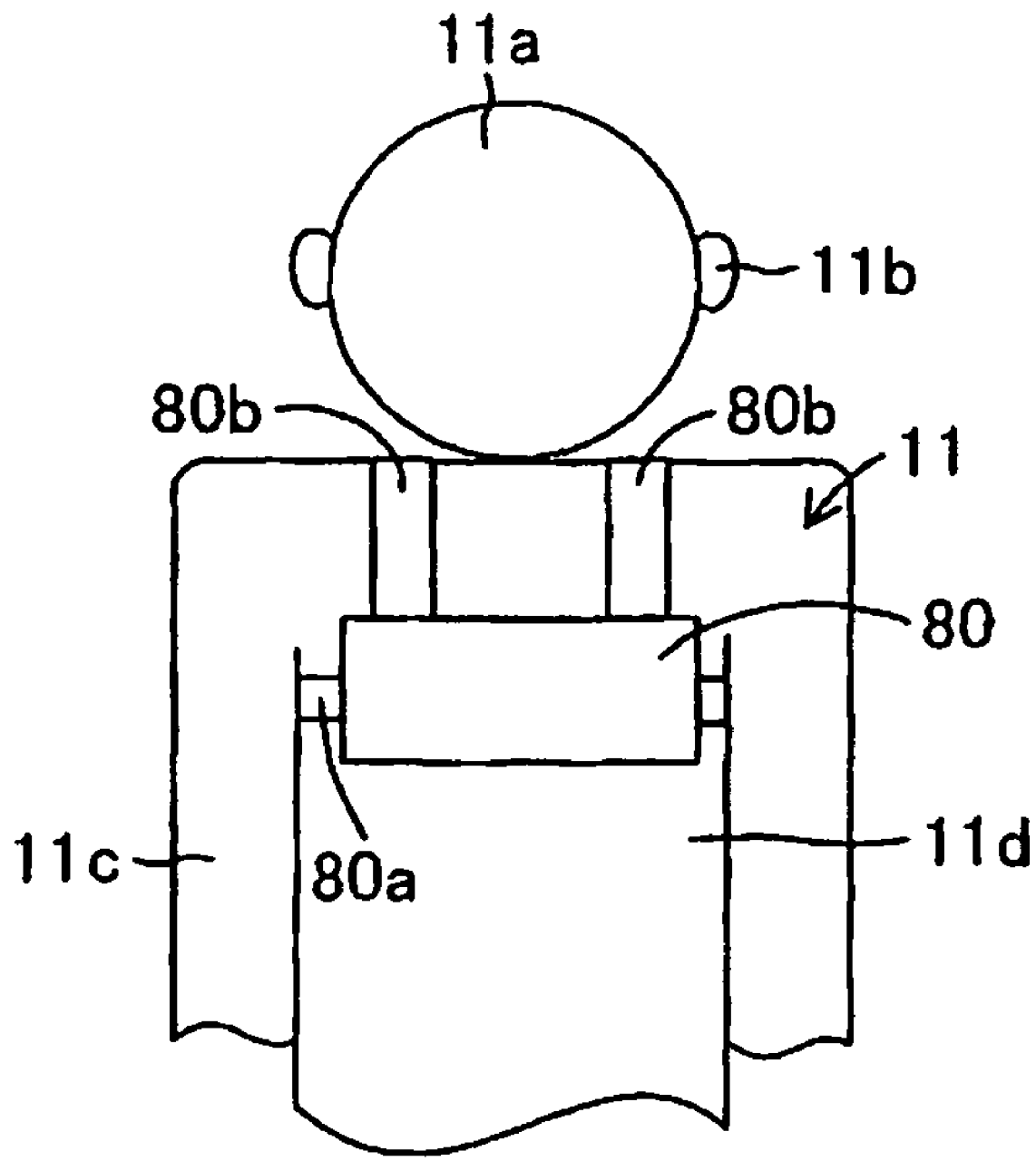
FIG. 11 diagrammatically a speech processor attached to the back of a human body.

FIG. 11 shows a speech processor 80 that is attached to a back 11d of the human body 11. The speech processor 80 is equipped with a middle belt 80a wound about the chest, and a pair of shoulder belts 80b hung on the shoulders. Details of the main unit of the speech processor 80 are designed identical to those of the speech processor 20. The speech processor 80 raises no obstacle to the user's motion; hence, the user having the speech processor 80 can move freely without having an uncomfortable feeling.

Various tests were conducted using various thermoelectric generators, which were configured by attaching different types of heat absorption layers to the aforementioned thermoelectric transducer module 26, wherein temperature differences between terminal ends of thermoelectric elements 33 as well as amounts of electricity were measured. Results are shown in Tables 1 to 5. Specifically, measurement was performed with respect to a temperature difference $\Delta T$ (K), which occurred between the terminal ends of the thermoelectric elements 33 in prescribed elapsed times after each heat absorption layer was brought into contact with the skin surface, and measurement was performed with respect to power (mW) generated by each thermoelectric generator. The results of the tests shown in Tables 1 to 4 were produced by changing materials forming heat absorption layers; and the results of the tests shown in Table 5 were produced by changing the thickness of the heat absorption layer composed of a resin.

TABLE 1

(resin layer: polyethylene: 5 mm)

| | Time | | | | |
|---|---|---|---|---|---|
| | 10 sec | 30 sec | 1 min | 2 min | 5 min |
| $\Delta T$ (K) | 1.5 | 1.2 | 1 | 1 | 1 |
| Power (mW) | 4.5 | 2.88 | 2 | 2 | 2 |

Table 1 shows the results of testing in which a heat absorption layer was composed of a polyethylene resin of 5 mm thickness. At the elapsed time of 10 seconds counted after the heat absorption layer was brought into contact with the skin surface, the temperature difference $\Delta T$ (K) reached 1.5 K, and the generated power reached 4.5 mW; at the elapsed time of 30 seconds, the temperature difference $\Delta T$ (K) reached 1.2 K, and the generated power reached 2.88 mW; thereafter, in the time period between the elapsed times of 1 minute and 5 minutes, the temperature difference $\Delta T$ (K) remained at 1.5 K, and the generated power remained at 2 mW.

TABLE 2

(rubber layer: nitrile rubber: 5 mm)

| | Time | | | | |
|---|---|---|---|---|---|
| | 10 sec | 30 sec | 1 min | 2 min | 5 min |
| ΔT (K) | 1.5 | 1.2 | 1 | 1 | 1 |
| Power (mW) | 4.5 | 2.88 | 2 | 2 | 2 |

Table 2 shows results of testing in which the heat absorption layer was composed of nitrile rubber of 5 mm thickness. The results of Table 2 produced using the nitrile rubber layer are identical to the results of Table 1 produced using the polyethylene resin layer.

TABLE 3

(metal layer: aluminum: 500 μm)

| | Time | | | | |
|---|---|---|---|---|---|
| | 10 sec | 30 sec | 1 min | 2 min | 5 min |
| ΔT (K) | 2.2 | 1.8 | 1.2 | 1 | 1 |
| Power (mW) | 9.68 | 6.48 | 2.88 | 2 | 2 |

Table 3 shows results of testing in which the heat absorption layer was composed of aluminum of 500 μm thickness. That is, at the elapsed time of 10 seconds counted after the heat absorption layer was brought into contact with the skin surface, the temperature difference ΔT (K) reached 2.2 K, and the generated power reached 9.68 mW; at the elapsed time of 30 seconds, the temperature difference ΔT (K) reached 1.8 K, and the generated power reached 6.48 mW; at the elapsed time of 1 minute, the temperature difference ΔT (K) reached 1.2 K, and the generated power reached 2.88 mW; thereafter, in the time period between the elapsed times of 2 minutes and 5 minutes, the temperature difference ΔT (K) remained at 1 K, and the generated power remained at 2 mW.

TABLE 4

(metal layer: magnesium alloy: 500 μm)

| | Time | | | | |
|---|---|---|---|---|---|
| | 10 sec | 30 sec | 1 min | 2 min | 5 min |
| ΔT (K) | 1.9 | 1.8 | 1.4 | 1 | 1 |
| Power (mW) | 7.22 | 6.48 | 3.92 | 2 | 2 |

Table 4 shows results of testing in which the heat absorption layer was composed of magnesium alloy of 500 μm thickness. That is, at the elapsed time of 10 seconds counted after the heat absorption layer was brought into contact with the skin surface, the temperature difference ΔT (K) reached 1.9 K, and the generated power reached 7.22 mW; at the elapsed time of 30 seconds, the temperature difference ΔT (K) reached 1.8 K, and the generated power reached 6.48 mW; at the elapsed time of 1 minute, the temperature difference ΔT (K) reached 1.4 K, and the generated power reached 3.92 mW; thereafter, in the time period between the elapsed times of 2 minutes and 5 minutes, the temperature difference ΔT (K) remained at 1 K, and the generated power remained at 2 mW.

TABLE 5

(resin layer: silicon: elapsed time of 5 minutes)

| | Thickness | | | | |
|---|---|---|---|---|---|
| | 1 mm | 2 mm | 5 mm | 6 mm | 7 mm |
| ΔT (K) | 1.2 | 1 | 1 | 0.8 | 0.7 |

Table 5 shows results of testing performed using thermoelectric generators having heat absorption layers composed of silicon resin, wherein the heat absorption layers were varied in thickness in a range between 1 mm and 7 mm. Specifically, measurement was performed with respect to the temperature difference ΔT (K) at the elapsed time of 5 minutes counted after the thermoelectric generators were each brought into contact with the skin surface. Table 5 shows ΔT at 1.2 K in the case of 1 mm thickness, ΔT at 1 K in the case of 2 mm thickness, ΔT at 1 K in the case of 5 mm thickness, ΔT at 0.8 K in the case of 6 mm thickness, and ΔT at 0.7 K in the case of 7 mm thickness.

In all the aforementioned tests, the thermoelectric generators are each constituted using the thermoelectric transducer module 26 and the heat absorption layer and not using any heat-dissipation member. Tables 1 to 4 clearly show that after 2 minutes elapse, the temperature difference ΔT remains at 1 K, and the generated power remains at 2 mW, irrespective of the materials of the heat absorption layers. It seems that the measurement values may remain the same even when the elapsed time is longer than 5 minutes in testing.

Within the elapsed time of 2 minutes, the generated power is higher when using metals for heat absorption layers compared with resin and rubber. As to the comparison between aluminum and magnesium alloy for use in the heat absorption layers, at the elapsed time of 10 seconds, the generated power is higher when using the aluminum layer; at the elapsed time of 30 seconds, the generated power is the same with respect to both the aluminum layer and magnesium alloy layer; and at the elapsed time of 1 minute, the generated power is higher when using the magnesium alloy layer.

Figure 5:
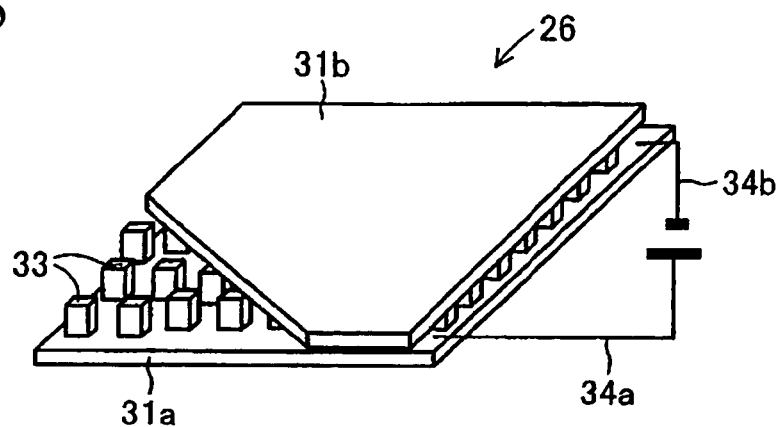
FIG. 5 is a perspective view partly in cross section showing a thermoelectric transducer module incorporated into the artificial inner ear.
Figure 6:
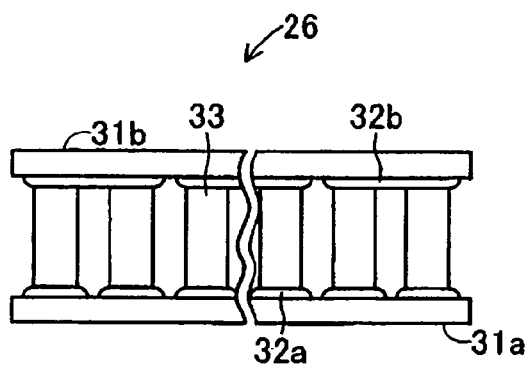
FIG. 6 is a front view partly in cross section showing the thermoelectric transducer module.

FIG. 5 clearly shows that at the elapsed time of 5 minutes, the generated power is higher as the thickness of the heat absorption layer is smaller; in other words, the generated power is lower as the thickness of the heat absorption layer is larger. It seems that the measurement values remain the same even when the elapsed time is longer than 5 minutes in testing.

Based on the aforementioned results of testing, it can be concluded that the thickness of the heat absorption layer composed of resin can be preferably set to 5 mm or less so as to produce the temperature difference ΔT of 1 K; and the thickness of the heat absorption layer composed of metal can be preferably set to 500 μm or less.

Next, other testing was performed using a thermoelectric generator in which a heat absorption layer composed of copper or aluminum was attached onto an upper substrate of a thermoelectric transducer module having a rectangular shape whose length and width were both set to 40 mm. Specifically, the testing was performed by attaching the aforementioned thermoelectric generator onto the subject person's wrist so as to examine whether or not the subject person felt uncomfortable, wherein the thermoelectric generator was adjusted such that at the elapsed time of 5 minutes, the temperature difference ΔT reached 1 K. The results show that with respect to the thermoelectric generator using a heat absorption layer composed of copper, two persons out of ten persons felt uncomfortable when the thickness of the heat absorption layer was increased to be 500 μm or more.

With respect to the thermoelectric generator using a heat absorption layer composed of aluminum, one person out of ten persons felt uncomfortable when the thickness of the heat absorption layer was increased to 500 µm or more.

The aforementioned results may clearly show that the thickness of the heat absorption layer composed of metal can be preferably decreased to 500 µm or less in order to avoid the uncomfortable feeling when the user attaches the thermoelectric generator.

The present invention regarding the thermoelectric generator and artificial inner ear is not necessarily limited to the aforementioned embodiment and modifications; that is, the present invention can be realized by any other variations. For example, the present embodiment uses polyethylene resin and silicon resin as resin materials for use in the formation of heat absorption layers; however, it is possible to use other resin materials such as nitrile resin, polystyrene resin, fluorine-contained resin, polypropylene resin, acrylic resin, urethane resin, ABS resin, epoxy resin, and polyamide resin.

Metal materials for use in the formation of heat absorption layers are not necessarily limited to aluminum and magnesium alloy; hence, it is possible to use aluminum alloy, magnesium, copper, and other metals. In addition, it is possible to use various rubber materials other than nitrile rubber for use in the formation of heat absorption layers. The present embodiment provides an example of the combination of different materials for use in the formation of heat absorption layers such as the heat absorption layer 78 consisting of the plastic layer 78a and aluminum layer 78b. Of course, it is possible to provide various combinations of different materials, wherein each combination is not necessarily composed of two different materials; hence, it is possible to provide combinations of three or more different materials for use in the formation of heat absorption layers. As described above, it is possible to freely set the thickness of heat absorption layers and to freely select materials for use in the formation of heat absorption layers.

Moreover, it is possible to use other materials such as a specific material in which metal powder is mixed with a resin or rubber for use in the formation of heat absorption layers. It may be preferable to use a resin or rubber whose thermal conductivity is $1.5 \times 10^{-1}$ W/mK or more for use in the formation of heat absorption layers; alternatively, it is possible to mix metal powder into the aforementioned resin or rubber. It may be preferable to use a resin or rubber whose modulus of tensile elasticity is 400 Kg/mm$^2$ or less for use in the formation of heat absorption layers; alternatively, it is possible to mix metal powder into the aforementioned resin or rubber.

The present embodiment and its modifications present various examples of thermoelectric generators particularly adapted to the artificial inner ear 10. Of course, the thermoelectric generator of the present invention is not necessarily applied to the artificial inner ear system and can be applied to other devices as their power sources. The thermoelectric generator of the present invention uses a heat source realized as the human body temperature; hence, it is preferably applied to human-body-aided devices. Furthermore, other parts of the thermoelectric generators and the artificial inner ear 10 can be appropriately changed in design and structure within the scope of the present invention.

Lastly, the present invention is not necessarily limited to the aforementioned embodiment and modifications; hence, any variations and further modifications within the scope of the invention are therefore intended to be embraced by the appended claims.

What is claimed is:

1. A thermoelectric generator including a thermoelectric transducer module in which a plurality of thermoelectric elements join between oppositely arranged first and second insulating substrates each having a plurality of electrodes so as to produce electricity in response to a temperature difference occurring between the first and second insulating substrates, said thermoelectric generator characterized in that a heat absorption layer composed of a heat conductive material having deformability in shape adapted to conform with a skin surface of a prescribed part of a human body is attached to one of the first and second insulating substrates.

2. A thermoelectric generator according to claim 1, wherein a heat-dissipation member composed of a prescribed metal is attached to the other of the first and second insulating substrates.

3. A thermoelectric generator according to claim 2, wherein the heat-dissipation member is composed of aluminum or aluminum alloy.

4. A thermoelectric generator according to claim 3, wherein the heat-dissipation member is connected with heat-dissipation wires.

5. A thermoelectric generator according to claim 1, wherein the heat absorption layer includes at least one of a resin layer those thickness is 5 mm or less, a rubber layer whose thickness is 5 mm or less, and a metal layer whose thickness is 500 µm or less.

6. A thermoelectric generator according to claim 1, wherein the heat absorption layer forms one of the first and second insulating substrates.

7. A thermoelectric generator according to claim 1 further comprising a battery for accumulating the electricity generated by the thermoelectric transducer module.

8. An artificial inner ear comprising:
a microphone for picking up sound;
a speech processor for performing speech processing so as to convert the sound picked up by the microphone into an audio signal;
a transmitter for transmitting the audio signal;
a receiver for receiving the audio signal; and
an electrode, implantable into a cochlea, for applying an electric impulse to an auditory nerve in response to the audio signal so as to make a brain sensitive to the sound,
wherein said speech processor operates using electricity generated by a thermoelectric generator including a thermoelectric transducer module in which a plurality of thermoelectric elements join between oppositely arranged first and second insulating substrates each having a plurality of electrodes,
and wherein a heat absorption layer composed of a heat conductive material having deformability in shape adapted to conform with a skin surface of a prescribed part of a human body is attached to one of the first and second insulating substrates.

9. The artificial inner ear incorporating a thermoelectric generator according to claim 8, wherein a heat-dissipation member composed of a prescribed metal is attached to the other of the first and second insulating substrates.

10. The artificial inner ear incorporating a thermoelectric generator according to claim 8, wherein the heat-dissipation member is composed of aluminum or aluminum alloy.

11. The artificial inner ear incorporating a thermoelectric generator according to claim 8, wherein the heat absorption layer includes at least one of a resin layer those thickness is 5 mm or less, a rubber layer whose thickness is 5 mm or less, and a metal layer whose thickness is 500 µm or less.

12. The artificial inner ear incorporating a thermoelectric generator according to claim 8, wherein the speech processor is attachable to the human body by way of a fitting member.

* * * * *